(12) United States Patent
Matsui et al.

(10) Patent No.: US 7,608,758 B2
(45) Date of Patent: Oct. 27, 2009

(54) PLANT SYSTEM FOR COMPREHENSIVE GENE FUNCTION ANALYSIS WITH THE USE OF FULL-LENGTH CDNA

(75) Inventors: Minami Matsui, Kanagawa (JP); Takanari Ichikawa, Kanagawa (JP); Miki Nakazawa, Kanagawa (JP); Motoaki Seki, Ibaraki (JP); Miki Fujita, Ibaraki (JP); Kazuo Shinozaki, Ibaraki (JP)

(73) Assignee: Riken, Saitama (JP)

( * ) Notice: Subject to any disclaimer, the term of this patent is extended or adjusted under 35 U.S.C. 154(b) by 299 days.

(21) Appl. No.: 10/488,087

(22) PCT Filed: Aug. 29, 2002

(86) PCT No.: PCT/JP02/08739

§ 371 (c)(1),
(2), (4) Date: Mar. 1, 2004

(87) PCT Pub. No.: WO03/018808

PCT Pub. Date: Mar. 6, 2003

(65) Prior Publication Data

US 2004/0203013 A1  Oct. 14, 2004

(30) Foreign Application Priority Data

Aug. 31, 2001  (JP) ............... 2001-264156

(51) Int. Cl.
  *C12N 15/82* (2006.01)
(52) U.S. Cl. ...................... 800/294; 800/278
(58) Field of Classification Search ........... None
  See application file for complete search history.

(56) References Cited

U.S. PATENT DOCUMENTS

| | | | | |
|---|---|---|---|---|
| 6,077,993 | A | * | 6/2000 | Mahajan ............ 800/278 |
| 6,174,669 | B1 | * | 1/2001 | Hayashizaki et al. ....... 435/6 |
| 6,407,312 | B1 | * | 6/2002 | Banno et al. ............ 800/278 |

FOREIGN PATENT DOCUMENTS

| WO | WO 99/36516 A2 | 7/1999 |
|---|---|---|
| WO | WO 00/01846 A2 | 1/2000 |
| WO | WO 01/07600 A1 | 2/2001 |

OTHER PUBLICATIONS

Seki M., et al., Functional annotation of a full-length *Arabidopsis* cDNA, collection., Science (Apr. 2002), vol. 296, No. 5565,, pp. 141-145.
LeClere S., et al., A library of *Arabidopsis* 35S-cDNA lines for identifying novel mutants., Plant Mol Biol. (Aug. 2001), vol. 46, No. 6, pp. 695-703.
Weigel D., et al., Activation tagging in *Arabidopsis*., Plant Physiol. (2000) vol. 122, No. 4, pp. 1003 to 1013.
Seki M., et al., High-efficiency cloning of *Arabidopsis* full-length cDNA by biotinylated CAP trapper,., Plant J. (1998), vol. 15, No. 5, pp. 707 to 720.
Carninci P., et al., Balanced-size and long-size cloning of full-length, cap-trapped cDNAs into vectors of the novel lambda-FLC family allows enhanced gene discovery rate and functional analysis., Genomics (Sep. 2001), vol. 77, No. 1-2, pp. 79 to 90.
M. Seki et al., "*Arabidopsis* encyclopedia using full-length cDNAs and its application", *Plant Physiol. Biochem.*, vol. 39, 2001, pp. 211-220.
M. Seki et al., "Monitoring the Expression Pattern of 1300 *Arabidopsis* Genes under Drought and Cold Stresses by Using a Full-Length cDNA Microarray", *The Plant Cell*, vol. 13, Jan. 2001, pp. 61-72.

* cited by examiner

*Primary Examiner*—David H Kruse
(74) *Attorney, Agent, or Firm*—Sughrue Mion, PLLC (57) ABSTRACT

A gene causative of a phenotype is easily specified and thus gene functions are comprehensively analyzed. A method for analyzing a gene function includes (a) infecting a plant group with a full-length cDNA library containing an expression regulatory sequence to introduce the cDNA into the plants; (b) selecting a plant complying with desired selection requirements from the plants into which the cDNA has been introduced; (c) isolating the cDNA from the selected plant; and (d) re-introducing the thus isolated cDNA into a plant of the same species as the plant into which the cDNA has been introduced, to reconfirm a phenotype according to the selection requirements.

6 Claims, 4 Drawing Sheets

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: PCR primer

<400> SEQUENCE: 1
acattctaca actacatcta gagg                                        24
```

```
<210> SEQ ID NO 2
<211> LENGTH: 16
<212> TYPE: DNA
<213> ORGANISM: Artificial Sequence
<220> FEATURE:
<223> OTHER INFORMATION: PCR primer

<400> SEQUENCE: 2
cggccgcccc ggggat                                                    16
```

PLANT SYSTEM FOR COMPREHENSIVE GENE FUNCTION ANALYSIS WITH THE USE OF FULL-LENGTH CDNA

This application is a 371 of PCT/JP02/08739, filed on Aug. 29, 2002; the disclosure of which is incorporated herein by reference.

TECHNICAL FIELD

The present invention provides a plant system for comprehensive gene function analysis with the use of full-length cDNAs.

BACKGROUND ART

To analyze gene functions, methods for introducing a point mutation or introducing an insertion or deletion mutation into a gene are conventionally employed. For the introduction of a point mutation, a method for chemically treating the whole genome with a mutation-inducing reagent is common. However, according to this method, one nucleotide substitution must be searched for from among nucleotide sequences constituting hundreds of millions of genomic DNAs though a mutation can easily be introduced, and therefore identification takes much time. Accordingly, it may be said that the method is unsuitable for determining the identification of functions of tens of thousands of genes comprehensively and at high speeds.

A gene tagging method is known as a method for introducing a mutation into a gene with high efficiency and examining gene function in a short period of time. According to this method, a known gene fragment (a tag) is inserted into a genome at random and a gene function at the insertion site is disrupted. For plants, a T-DNA or a transposon is used as such a gene tag (Krysan, P. J. et al., Plant Cell, 1999. 11(12): pp. 2283-90; Speulman E. et al., Plant Cell, 1999. 11(10): pp. 1853-66). A gene fragment is randomly inserted into a genome by infection of a plant with *Agrobacterium* and by crossing with a plant having transposase, in the cases of a T-DNA and a transposon, respectively. Then, one or two copies of T-DNA are usually inserted per plant individual (Azpiroz-Leehan, R. et al., Trends Genet, 1997. 13(4): pp. 152-6), and in the case of a certain type of transposon, one copy thereof is inserted into a genome (Fedoroff, N. et al., Bioessays, 1995. 17(4): pp. 291-7). By preparing tens of thousands of such insertion mutation strains, a group of plant strains wherein individual gene functions are disrupted can be produced.

A plant exhibiting a mutant character of interest is isolated and thereafter the relationship between the mutant character and the gene is examined. In such case, genetic information adjacent to the insertion site can be obtained by methods such as PCR using the introduced gene fragment as a clue, and thereby gene function can be identified comprehensively and at high speeds (Krysan, P. J. et al., Plant Cell, 1999. 11(12): pp. 2283-90; Speulman, E. et al., Plant Cell, 1999. 11(10): pp. 1853-66).

As an improved form of this gene tagging method, an activation tagging method is known. This activation tagging method can bring about the transcriptional activation of a gene existing adjacent to the genome, into which the T-DNA has been inserted, by the use of a transcriptional enhancer sequence incorporated into the T-DNA. In recent years, this method has been developed as a new analytical method regarding plant gene functions (Walden, R. et al., Plant Mol Biol, 1994. 26(5): pp.1521-8). Among the features of this activation tagging method, a feature for enabling the production of a dominant mutation by a tag is considered to be the most important. In other words, it is possible to observe even a phenotype attributable to a gene mutation of a type having an overlapping function with other genes (e.g., gene group constituting a gene family). This feature has never been observed through the production of a conventional gene disrupted type of mutant.

However, there is one significant problem when such activation tagging method is used for comprehensive analysis of gene functions (analyzing gene functions existing on a genome in a group). That is, a genome region that can potentially be transcriptionally activated is extended to approximately 5 kb backward and forward from the insertion site since the enhancer sequence is used as an activator inside the tag (Weigel, D. et al., Plant Physiol, 2000. 122(4): pp. 1003-13). Since two or more genes are present on average in a genome region of 10 kb in a model plant like *Arabidopsis thaliana*, it is difficult to determine which gene is activated by the enhancer. Therefore, in order to specify a causative gene, these genes adjacent to the insertion site are all isolated and transformations thereof are carried out again for enforced expression, so that the reproduction of the phenotype is confirmed. Through this confirmation, it is essential to examine which gene has functioned to define the phenotype. This means that time on a yearly scale is required on average for analyses from the isolation of a plant exhibiting a trait of interest to the specification of a causative gene. Accordingly, in an attempt to use the activation tagging method for comprehensive analysis of genomic gene functions, the novelty of the obtained gene species or phenotype can be recognized. However, a significant contradiction that merits such as rapid specification of a gene and applicability to comprehensive analysis cannot be obtained, which can be found in the case of a conventional tagging method which is a gene disrupted type.

The present invention has an object to provide a next-generation activation tagging system, whereby a causative gene of a phenotype can easily be specified and gene functions can be comprehensively analyzed.

DISCLOSURE OF THE INVENTION

The present inventors have undertaken intensive studies to solve the above problems. As a result, they have successfully achieved comprehensive analysis of gene functions by introducing into a plant group *Agrobacterium* having a T-DNA vector containing a full-length cDNA and a promoter capable of constitutively or conditionally inducing expression in a plant cell; overexpressing the full-length cDNA; and confirming a phenotype of the transformed plant body, thus completing the present invention.

Namely, the present invention is as follows.

(1) A Method for Analyzing a Gene Function Comprising the Steps of:

(a) infecting a plant group with a full-length cDNA library containing an expression regulatory sequence to introduce the cDNA into the plants;

(b) selecting a plant complying with desired selection requirements from the plant group having the cDNA introduced thereinto;

(c) isolating the cDNA from the selected plant;

(d) re-introducing the isolated cDNA into a plant of the same species as the plant into which the cDNA has been introduced to reconfirm a phenotype according to the selection requirements.

(2) A System for Analyzing a Gene Function Comprises:

(a) means for infecting a plant group with a full-length cDNA library containing an expression regulatory sequence to introduce the cDNA into the plants;

(b) means for selecting a plant complying with desired selection requirements from the plant group having the cDNA introduced thereinto;

(c) means for isolating the cDNA from the selected plant;

(d) means for re-introducing the isolated cDNA into a plant of the same species as the plant into which the cDNA has been introduced to reconfirm a phenotype according to the selection requirements.

In the above analytical method and system, as the expression regulatory sequence, a constitutive expression promoter, an inducible promoter or a combination thereof may be exemplified. Further, a full-length cDNA library that is introduced into *Agrobacterium* can be used. In this case, the cDNA is introduced into a plant by infection of *Agrobacterium*.

Further, as the selection requirements, morphogenetic mutation and/or stress resistance may be given. As a stress, exemplified is at least one form of stress selected from the group consisting of oligotrophic stress, drought stress, temperature stress (low temperature or high temperature stress), strong light stress, ultraviolet stress, salt stress, air pollution stress, agricultural chemical stress, oxidization stress, heavy metal stress, disease damage stress, and hormone stress.

(3) A Plant Containing a Gene Having a Function Analyzed by the Above Analytical Method.

The above plant includes any plant selected from the group consisting of a plant body, a seed, a callus, and a protoplast.

Figure 1:
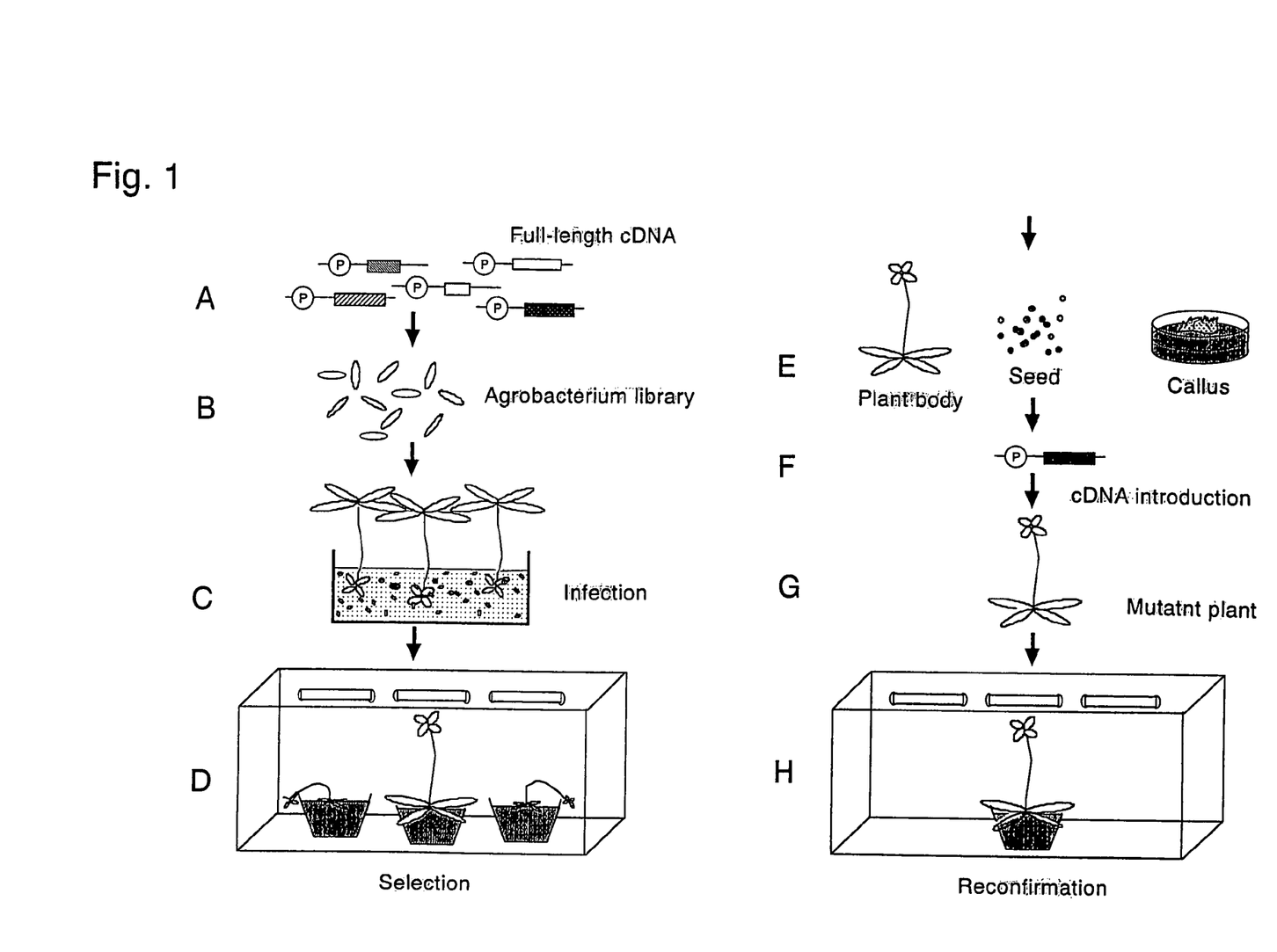
FIGS. 1A-1H are views illustrating the outline of the method of analyzing gene functions using a full-length cDNA according to the present invention.

The present invention is a method for analyzing gene functions of plants as a group, without conducting gene analysis of each plant, by introducing a full-length cDNA into a plant group, and confirming a phenotype of the plant group. The present inventors named this method the "Fox Hunting System" (Full-length cDNA over-expression gene hunting system). This method will be described hereinafter (FIG. 1).

(1) Means for Preparing a Full-Length cDNA Library (FIG. 1A)

A full-length cDNA used for the present invention is defined as a complete copy of mRNA. Even when a cDNA longer than the obtained cDNA is present, such cDNA is included in the full-length of cDNA of the present invention.

A full-length cDNA library includes information on all the amino acids indispensable when a gene functions, and therefore all the functions originally owned by the genes to be introduced can be exhibited. Accordingly, in comparison with conventional cDNA libraries, the full-length cDNA library has higher efficiency in terms of functional expression. Further, since all the cDNA fragments have original information on an initiation codon and a stop codon, protein fusion for expression is not necessary and the efficiency for protein expression is high.

Such a full-length cDNA can efficiently be prepared from an mRNA of interest by methods known to a person skilled in the art. At the 5' terminus of mRNA, 7-methylguanosine is added through a 5',5' triphosphate linkage. By focusing attention on this point, several technologies for full-length cDNA synthesis have been developed. Methods usable for the present invention include, but are not limited to, the Cap-trapper method (Carninci, P., et al., Genomics, 1996. 37(3): pp. 327-36) and the Cap-finder method (Zhao, Z., et al., J. Biotechnol., 1999. 73(1): pp. 35-41).

As a vector for cloning a full-length cDNA, it is preferable to use a vector such as SfiI, which recognizes eight or more nucleotides and has restriction enzyme sites at both sides of the cDNA insertion site for defining the direction of inserted DNA to one way.

A full-length cDNA library carrying the above full-length cDNA can be prepared by using methods known to a person skilled in the art. Examples of vectors for preparing the library include pTAS and pBIG2113SF.

Further, the full-length cDNA library used for the method of the present invention can be prepared by using mRNAs derived from various organisms. For example, cDNA may be synthesized from mRNAs of yeasts, plant pathogens, or the like, in addition to useful plants such as *Arabidopsis thaliana*, tomatoes, rice plants, and corn.

Plants are higher organisms from which transformant clones are very easily produced. Transformants obtained therefrom are suitable for the production of seeds as resource. Therefore, it is preferable to prepare a full-length cDNA library from a plant.

Further advantageously, even if a plant is infected with a library including hundreds of million of clones, only one or two clones are introduced into one plant and thus the transformed plants are introduced with different clones.

On the other hand, a higher animal cell is intracellularly partitioned by various membrane structures in the same manner as a higher plant cell, and similarities therebetween have been found to a surprising degree in terms of mechanisms for maintenance of such structures or mechanisms for intracellular signal transduction. Therefore, a full-length cDNA library can be prepared from mRNAs derived from animals. This means that it is possible to identify functions of animal genes that are common with a higher plant by introducing a full-length cDNA derived from a higher animal into a higher plant. It is confirmed that many genes of *Arabidopsis thaliana* exhibit high homology with human genes. For example, it has been known that genes similar to 169 genes of 289 genes which are causative genes for human genetic diseases that have been identified so far are present on the genome of *Arabidopsis thaliana*, and these genes have high homology (Tabata, Kagaku-to-seibutu (Chemistry and Biology), Vol., 39, No. 6, 2001).

Since all the mRNA molecules are substituted with cDNA molecules at an equivalent quantitative ratio in a conventional cDNA library, groups of structural protein genes having high level of expression account for large part of molecules in the library. In contrast, groups of genes such as those associated with signal transduction often account for an extremely small portion in the library since those gene groups usually have low expression levels. Thus, the abundance ratios of individual cDNA clones are largely varied depending on the gene expression level. It is then preferable to prepare a library so that all the clones are contained therein at equivalent ratios regardless of the gene expression level. Preparing such library is referred to as "normalization."

When an equivalent amount of each clone from this full-length cDNA is mixed, a normalized full-length cDNA mixture can be obtained. The 5' and 3' terminal sequences of the synthesized full-length cDNAs are determined, and thereby full-length cDNA clones having no overlapping (there are no common sequences in a partial region at termini) where terminals do not have a common sequence in a partial region thereof) are selected. Based on the results, a database is made.

The normalized full-length cDNA library is constructed by selecting cDNAs different from each other and mixing them in equivalent amounts. Thus, it is uniform on the whole in terms of molecular species although conventional cDNA libraries have nonuniformity. Accordingly, when a multicopy gene group of a genomic gene is taken into account, the functions of different genes can be examined more fairly, that is, with higher efficiency, than in a case where tagging of genome is carried out.

Further, normalized full-length cDNAs corresponding to 50% or more of the entire genome are provided for *Arabidopsis thaliana*. With respect to human genes, normalized full-length cDNAs corresponding to approximately 80% or more of the entire genome are present. A resource of the same type as above is being prepared for rice, a useful plant. Accordingly, these provided normalized full-length cDNAs can also be used for the present invention.

However, the normalization of a full-length cDNA library is not always necessary for the method of the present invention. Whether or not the normalization is carried out can be properly determined by a person skilled in the art based on various factors and cost, such as the extent to which the genomic information of a target organism is known or the expected expression level of a target gene. For example, when a person wishes to analyze the function of a structural protein, a conventional full-length cDNA library is sufficient for analysis since a gene for that protein is considered to be highly expressed.

(2) Means for Cloning a Full-Length cDNA into an Expression Vector (FIG. 1B)

The obtained full-length cDNA or normalized full-length cDNA is cloned into a T-DNA expression vector used for plant transformation with *Agrobacterium tumefaciens*. T-DNA is a specific region of a Ti plasmid, which is found in a pathogenic strain of *Agrobacterium*, pathogenic bacteria of crown gall, which is a form of dicotyledon tumor. When a plant is infected with these bacteria, T-DNAs are transferred into plant cells to be incorporated into a genomic DNA.

This T-DNA contains a sequence for regulating the expression of the full-length cDNA therein. As an expression regulating sequence, a cassette wherein a terminator is ligated to a promoter sequence that constitutively or conditionally induces expression in a plant cell is preferably incorporated. Preferable constitutive expression promoter sequence include a 35S promoter sequence of Cauliflower Mosaic Virus (Sanders, P. R. et al., Nucleic Acids Res, 1987. 15(4): pp. 1543-58). Examples of inducible promoters include glucocorticoid inducible promoter sequence (Aoyama, T. et al., Plant J, 1997. 11(3): pp. 605-12), estrogen inducible promoter sequence (Zuo, J. et al., Plant J, 2000. 24(2): pp. 265-273). According to the present invention, these promoters may arbitrarily be combined (ligated) with each other for use. Combinations may be made between constitutive expression promoters, between inducible promoters, or between both constitutive expression and inducible promoters.

The aforementioned full-length cDNA or normalized full-length cDNA is inserted into the downstream of the promoter sequence in the sense or antisense direction through enzymatic reaction. When a sense chain is expressed by this insertion, changes of a phenotype caused by overexpression of a gene encoding the inserted cDNA can be observed. When an antisense chain is expressed, changes of the phenotype caused by underexpression of a gene encoding the inserted cDNA can be observed.

(3) Means for Transducing a Full-Length cDNA Library into a Plant (FIG. 1C)

Next, a group of T-DNAs (a Full-length cDNA over-expressor library; FOX library) wherein this full-length cDNA has been inserted is introduced into *Agrobacterium* by a conventional method to produce a library. Thereafter, cDNAs in the library are introduced (for transformation) into a plant through infection with Agrobacterium.

Plants to be infected with *Agrobacterium* may be either dicotyledon or monocotyledon. However, when monocotyledon is used, addition of a phenolic compound (acetosyringone) to a medium is preferable for efficient infection with *Agrobacterium*.

Plants as described above mean all of entire plant bodies, plant organs (e.g., leaves, flower petals, stems, roots, and seeds), plant tissues (e.g., epidermis, phloems, parenchymas, xylems, and vascular bundles), or cultured plant cells (including protoplasts and calluses).

Plants to be used for transformation include, but are not limited to, those belonging to Brassicaceae, Gramineae, Solanaceae, and Leguminosae (see below).

Brassicaceae: *Arabidopsis thaliana*

Solanaceae: *Nicotiana tabacum*

Gramineae: *Zea mays, Oryza sativa*

Leguminosae: *Glycine max*

A dipping method may be employed for infection of a plant with *Agrobacterium*. In the case of using a dipping method, a bundle of plant bodies are dipped in a liquid containing *Agrobacterium* for 30 to 60 seconds. If necessary, cells prepared by tissue culture may be co-cultured.

Individual *Agrobacterium* in the library have vectors (T-DNA) into which different cDNAs have been inserted, and one or two copies of T-DNA are usually inserted per single plant individual. Therefore, it is said that a group of these transformed plants are a group of plant clones, all of which can strongly express one to two different full-length cDNAs. Among the group of these plant individuals, a mutant of interest is selected by several methods described below.

(4) Selection Means by Phenotype (FIG. 1D)

While a group of plants having overexpressive cDNAs introduced thereinto is subjected to selection at T1 generation in accordance with antibiotic resistance, various kinds of stress resistance are additionally used to select a surviving (adaptable) mutant strain alone (referred to as "tailor made screening").

Further, a method can be employed wherein a callus prepared by tissue culture of a wild type plant is infected with the above *Agrobacteria* FOX library by a co-culture method. When the co-culture method using tissue culture is used, selection based on transformation and phenotype can be carried out at the same time. Thus, it is possible to use as a transformation material a plant that has poor transformation efficiency by dipping.

According to the above selection method, a mutant of interest can easily be obtained by conducting a search regarding functions of the entirety of the genes of the library as a group. This does not require the preparation of a full set of plant group containing the full-length cDNA at one time, which is referred to as "lining up". Therefore, it is possible with slight labor to screen genes capable of imparting specific properties (it does not matter whether functions are originally owned by that gene).

Furthermore, a plant is transformed using the *Agrobacterium* FOX library and seeds are harvested from the transformed plant. Thereafter, the entirety of the transformants that have become antibiotic-resistant are grown and seeds from individual plants are collected. The group of the thus collected seeds (seed library) can be used as material to conduct screening, which uses various phenotypes as indexes.

Plants of interest by phenotype can be isolated by various selection conditions such as resistances to various forms of stress, morphogenetic mutations, environment-responsive mutations, and secondary metabolite mutations. In this case, plants include plant bodies, seeds, and calluses (FIG. 1E).

Examples of forms of stress include oligotrophic stress, drought stress, temperature stress (low temperature or high temperature stress), strong light stress, ultraviolet stress, salt stress, air pollution stress, agricultural chemical stress, oxidation stress, heavy metal stress, disease damage stress, and hormone stress. These stresses may be applied either alone or in combination.

"Oligotrophic stress" means a form of stress caused by the lack of at least one of nitrogen, phosphoric acid, or potassium as major soil nutrient components, or by a decrease thereof to 50% or less of their usually required amounts.

"Drought stress" means a form of stress resulting when a continuous or temporary impact is given by the depletion of the water.

"Temperature stress" means a form of stress resulting when a plant is placed at a temperature higher or lower than the optimal temperature for plant growth. For example, "high temperature stress" is defined as a form of stress caused by a continuous or temporary impact of conditions where the temperature is 42° C. or higher for several minutes or longer. "Low temperature stress" is defined as a form of stress caused by a continuous or temporary impact of conditions where the temperature is −4° C. or lower for several minutes or longer.

"Strong light stress" is defined as a form of stress resulting when a plant is irradiated with a strong light beyond its photosynthesis ability, and it is a case, for example, when a light with 1000 to 2000 $\mu mol/s/m^2$ or more is radiated.

"Ultraviolet stress" means a form of stress resulting when a plant is placed under a state wherein ultraviolet irradiation (1 to 10 $mJ/cm^2$ min. or more) with a wavelength of 100 to 400 nm is carried out.

"Salt stress" means a form of stress caused when physiological functions of a plant are damaged as in a case wherein a plant cannot absorb water since the water potential decreases due to salts accumulated in soil. Examples of this form of stress include a form of stress caused by salt damage that is brought about through irrigation in a dry region.

"Air pollution stress" means a form of stress given by a continuous or temporary impact of air pollutants (ozone, sulfur dioxide, COX, etc.).

"Agricultural chemical stress" means a form of stress resulting when a plant comes into continuous or temporary contact with agricultural chemicals.

"Oxidation stress" means a form of stress caused by active oxygen.

"Heavy metal stress" means growth inhibition caused by the increase of concentrations of heavy metals in soil, such as aluminum, copper, zinc, nickel, manganese, or cadmium.

"Disease damage stress" means a form of stress caused when a plant suffers damage due to viruses, fungi, or insects, and examples thereof include blast disease, powdery mildew, brown leaf rust, Granville wilt, mosaic disease, and root rot.

"Hormone stress" means a form of stress caused when various plant hormones or environmental endocrine disruptors induce morphological abnormalities or metabolism abnormalities.

These stress-resistant plants are created by selecting plants that do not die but exhibit resistance to sufficiently stressful conditions for plants (e.g., no watering for one week or culturing at 37° C. or higher).

Further, "morphological mutation" means a mutation that induces morphogenesis different from that of a wild type of plant under its normal environment. Examples of plants wherein morphological mutation has occurred include plants with turions, dwarfed plants, plants having upsized leaves, and plants having well-running roots.

"Environment-responsive mutation" means a mutation occurring in response to any environmental signal usually detected by plants such as temperature, light or gravity. Examples of plants wherein environment-responsive mutation has occurred include plants that produce easy-to-germinate or difficult-to-germinate seeds, plants that can or cannot initiate the formation of flower bud immediately, and plants that bend or do not bend toward as following the direction of light or gravity.

"Secondary metabolite mutation" means a mutation wherein the amount of the entirety of secondary metabolites or a specific secondary metabolite produced by plants increases or decreases. In this connection, raw materials of many Chinese herbal medicines are derived from particular plants having such mutations.

In addition, mechanisms may exist whereby a plant exhibits a specific phenotype by the introduction of a full-length cDNA. When a sense mRNA is expressed, it is considered that a larger amount of normal protein than usual or normal protein in a tissue wherein the protein is not usually produced is produced because of its strong expression, thereby resulting in the appearance of a specific phenotype. It is further considered that the silencing effect of the sense mRNA decreases the amount of normal protein, thereby resulting in the appearance of a specific phenotype. In contrast, in the case of an antisense mRNA, it is thought that decreased expression of normal protein results in the appearance of a specific phenotype. An important point herein is that the specific phenotype appears as a dominant or semidominant phenotype regardless of mechanisms according to the system of the present invention. Therefore, changes of phenotype are considered attributable to the introduced full-length cDNA.

(5) Means for Reconfirming a Phenotype and Identifying a Gene Causative of a Mutant Character (Phenotype) (FIGS. 1F to H)

Next, a genomic DNA is extracted from the isolated transformed plant, and primers are designed from this DNA, based on information on a nucleotide sequence adjacent to a promoter sequence and terminator sequence contained in a T-DNA. Using these primers, PCR is carried out and a cDNA located between these transcriptional control regions is isolated (FIG. 1F). This cDNA is inserted into a T-DNA having the same promoter and terminator sequences as above, and the T-DNA is re-introduced into a normal plant of the same species as the transformed plant that had been isolated previously (FIG. 1G). The phenotype of stress resistance is thereby reconfirmed (FIG. 1H). Then, the sequencing of the cDNA enables the identification of a gene causative of a mutant character.

In the introduction of the full-length cDNA into a plant with *Agrobacterium*, the number of introduced copies of the full-length cDNA is one or two. Therefore, it is sufficient that a process for isolating the cDNA and confirming the phenotype is repeated at most twice, so that labor-saving and efficiency improvement can be achieved.

BEST MODES FOR CARRYING OUT THE PRESENT INVENTION

The present invention will hereinafter be described in detail with reference to Examples. However, the technical scope of the present invention is not limited to these Examples.

Example 1

Gene Function Analysis

In this example, cDNAs that induce mainly visible phenotypes such as morphological abnormalities were screened using pBIG2113SF prepared by introducing an SfiI cloning site into a constitutive expression vector pBIG2113N (Taji, T. et al., Plant J., 2002, 24(4): pp. 417-426, and Becker, D. et al. Nucleic Acid Res., 1990, 18(1): pp. 203).

(1) Preparation of Normalized Full-Length cDNA Mix

Full-length cDNAs were prepared from *Arabidopsis* by the CAPtrapper method. The cDNA was cloned at site flanked by SfiI restriction enzyme sites of Lambda ZAP or Lambda pLC-1-B (Seki M. et al. Plant J., 15, pp. 707-720 (1998)). Using a vector sequence, 5'- and 3'-termini of the cDNA were determined, grouping of the cDNAs was carried out, and 13,000 types of independent clones were identified (Seki M. et al. Plant Physiol. Biochem. 39, pp. 211-220 (2001)). Next, 0.5µ of each clone that was prepared to 50 ng/µl was collected and all of them were mixed into a single test tube. Then, 1 µl of the mixture solution was collected and 20 µl of Electric (Electroporation) competent cells DH10B (Gibco BRL) were transformed. Approximately 200,000 independent colonies grown on agar media containing Amp were mixed, and plasmids were collected therefrom. The obtained product is referred to as a normalized full-length cDNA mix.

(2) Preparation of FOX *Agrobacteria* Library

Two µg of the normalized full-length cDNA mix and 700 µg of pBIG2113SF were mixed and cleaved with SfiI at the same time. After the cleavage the obtained product was concentrated by isopropanol precipitation. Then, the concentrated product was dissolved in 8 µl of water and mixed with 1 µl of 10× buffer and 1 µl of T4 ligase for reaction for 24 hours at 16° C. Thereafter, 2 µl of the reaction solution was mixed with 40 µl of Electric competent cells DH10B to be transformed.

Approximately 150,000 independent colonies grown on agar media containing Kanamycin (Km) were mixed and plasmids were collected therefrom. Then, 2 µl of the collected plasmid solution was mixed into 40 µl of Electric competent *Agrobacterium* cells GV3101 to be transformed. Approximately 150,000 independent colonies grown on agar media containing Km were suspended in an LB liquid medium and glycerol was added so as to result in a concentration of 15%. The resultant product was stored at −80° C. This glycerol solution is referred to as a FOX *Agrobacteria* library.

(3) Preparation of FOX Line

Using the above FOX *Agrobacteria* library, approximately 200,000 colonies were grown and suspended in a dipping solution. Then, wild-type *Arabidopsis* (ecotype: Colombia) was dipped in the solution. The seeds from the plants were harvested, and germinated in an oligotrophic medium BAM containing hygromycin. Approximately 800 lines of plants exhibiting hygromycin resistance were selected and transplanted in soil.

(4) Phenotype Screening

Among approximately 800 lines, approximately 90 lines were selected having clear morphological differences from wild types or pigment abnormalities, which could be observed by the naked eye. Representative phenotypes included dwarfing or enlargement of plant bodies, pigment abnormalities of plant bodies, branching abnormalities, morphological abnormalities of leaves and inflorescences, and fertile abnormalities.

(5) Recloning of cDNA

Among 90 lines expressing these phenotypes, approximately two rosette leaves (approx. 200 mgfw) were collected from each of 47 lines, and genomic DNAs were extracted therefrom. PCR on these DNAs was carried out. A PCR reaction solution having the composition below was used and the reaction was carried out through 40 cycles of PCR, each cycle consisting of 30 seconds at 94° C., 30 seconds at 58° C., and 3.5 minutes at 68° C.

| Composition of reaction solution | |
|---|---|
| Primers (100 pM) | 2 × 0.5 µl |
| dNTP (200 µl) | 5 µl |
| Buffer (×10) | 5 µl |
| Polymerase | 1 µl |
| Genomic DNA | 10 µl |
| Distilled water | 28 µl |
| Total | 50 µl |

The primers for PCR were as follows.

```
GS4:   ACATTCTACAACTACATCTAGAGG   (SEQ ID NO: 1)

GS6:   CGGCCGCCCCGGGGAT           (SEQ ID NO: 2)
```

The PCR products were collected from agarose gel, mixed with pBIG2113SF, and then completely cleaved with SfiI. Then, the products were precipitated with isopropanol and treated with T4 ligase. With the obtained product, *E. coli* was transformed. Plasmids having PCR fragments inserted thereinto were selected, and the nucleotide sequences of inserted cDNA fragments were identified using GS4 or GS6.

(6) Full-Length cDNA Inserted into FOX Line

From 40 lines in which cloning was successfully carried out, 43 types of full-length cDNA sequences were found. As shown in Table 1, 42 types of them each had different sequences and were found to be inserted directly downstream of promoters of vectors.

TABLE 1

| line | fragment number | mips code | annotation |
|---|---|---|---|
| F00521 | | At5g27150 | NHE1 Na+/H+ exchanger |
| F00602 | | At1g08460 | hypothetical protein |
| F00718 | | At2g20880 | AP2 domain transcription factor |
| F00721 | | At3g16400 | putative lectin |
| F00732 | | At5g50700 | 11-beta-hydroxysteroid dehydrogenase-like |
| F00830 | | At5g54270 | Lhcb3 chlorophyll a/b binding protein |
| F00935 | | At3g28670 | unknown protein |
| F01022 | | At1g15820 | hypothetical protein |
| F01027 | | At4g27170 | NWMU4-2S albumin 4 precursor |
| F01049 | | At4g13930 | hydroxymethyltransferase |
| F01205 | | At3g43810 | calmodulin 7 |
| F01305 | | At1g62500 | putative proline-rich cell wall protein |
| F01310 | | At3g25920 | 50S ribosomal protein L15, chloroplast precursor |
| F01317 | 1 | At3g60830 | Actin like protein |
| F01325 | | | S-adenosylmethionine decarboxylase |
| F01407 | | At5g63850 | amino acid transporter AAP4 |
| F01408 | | At5g59090 | cucumisin precursor-like |
| F01410 | | At4g35260 | NAD+ dependent isocitrate dehydrogenase subunit 1 |
| F02304 | | At2g45560 | putative cytochrome P450 |
| F02318 | | At1g76180 | hypothetical protein (dehydrin like) |
| F02347 | | At1g66820 | hypothetical protein |
| F02510 | | At2g30590 | unknown protein |
| F02607 | 2 | At2g32210 | unknown protein |
| F02623 | 2 | At5g54180 | putative protein |
| F02635 | 2 | At3g01160 | hypothetical protein |
| F02742 | | At4g00100 | putative ribosomal protein S13 |
| F02813 | | At2g46540 | expressed protein |
| F03039 | | At5g43560 | unknown protein |
| F03048 | 3 | At2g46280 | Eukaryotic translation initiation factor 3 delta subunit |
| F03124 | | At2g43100 | 3-isopropylmalate dehydratase, small subunit |
| F03142 | 2 | At3g19516 | hypothetical protein |
| F03205 | | At1g23060 | unknown protein |
| F03208 | | At2g36970 | putative glucosyltransferase |
| F03209 | | At5g07990 | flavonoid 3'-hydroxylase-like protein |
| F03213 | | At3g10020 | unknown protein |
| F03215 | 1 | At3g45140 | lipoxygenase AtLOX2 |
| F03218 | 4U | At2g16080 | putative protein |
| F03218 | 4L | At3g16640 | Translationally controlled tumor protein-like protein (TCTP homologu) |
| F03224 | 2 | At5g56420 | putative protein |
| F03224 | 3 | At2g10940 | unknown protein |
| F03232 | | At5g47610 | putative protein |
| F23 | L | At5g49940 | nifU like protein |

Figure 2:
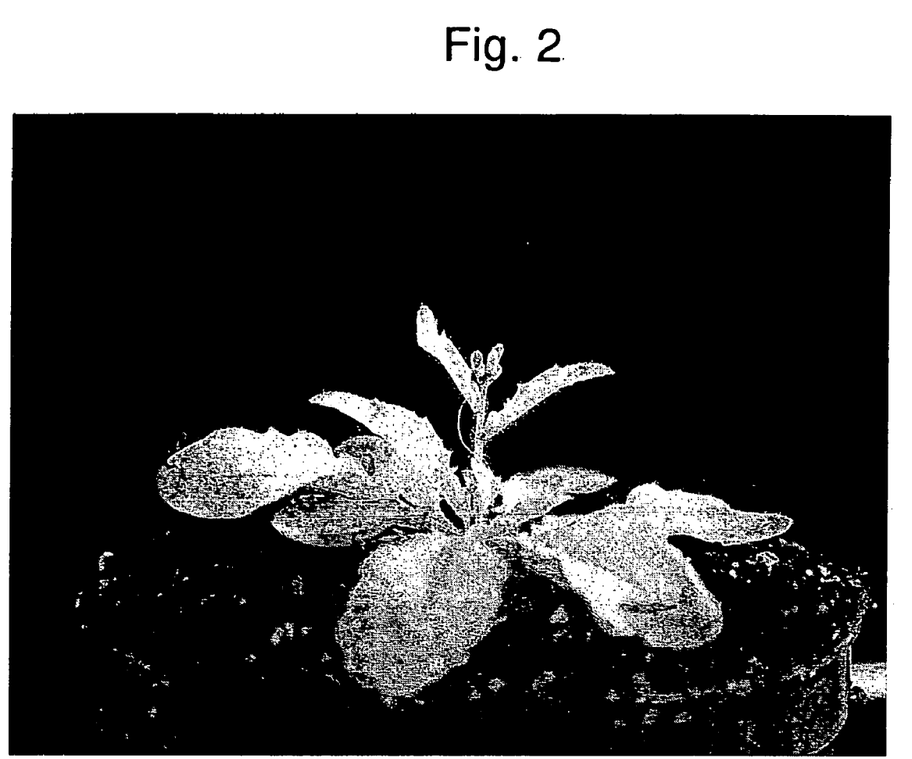
FIG. 2 is a photograph showing a T1 plant body of the F03024 line.
Figure 3:
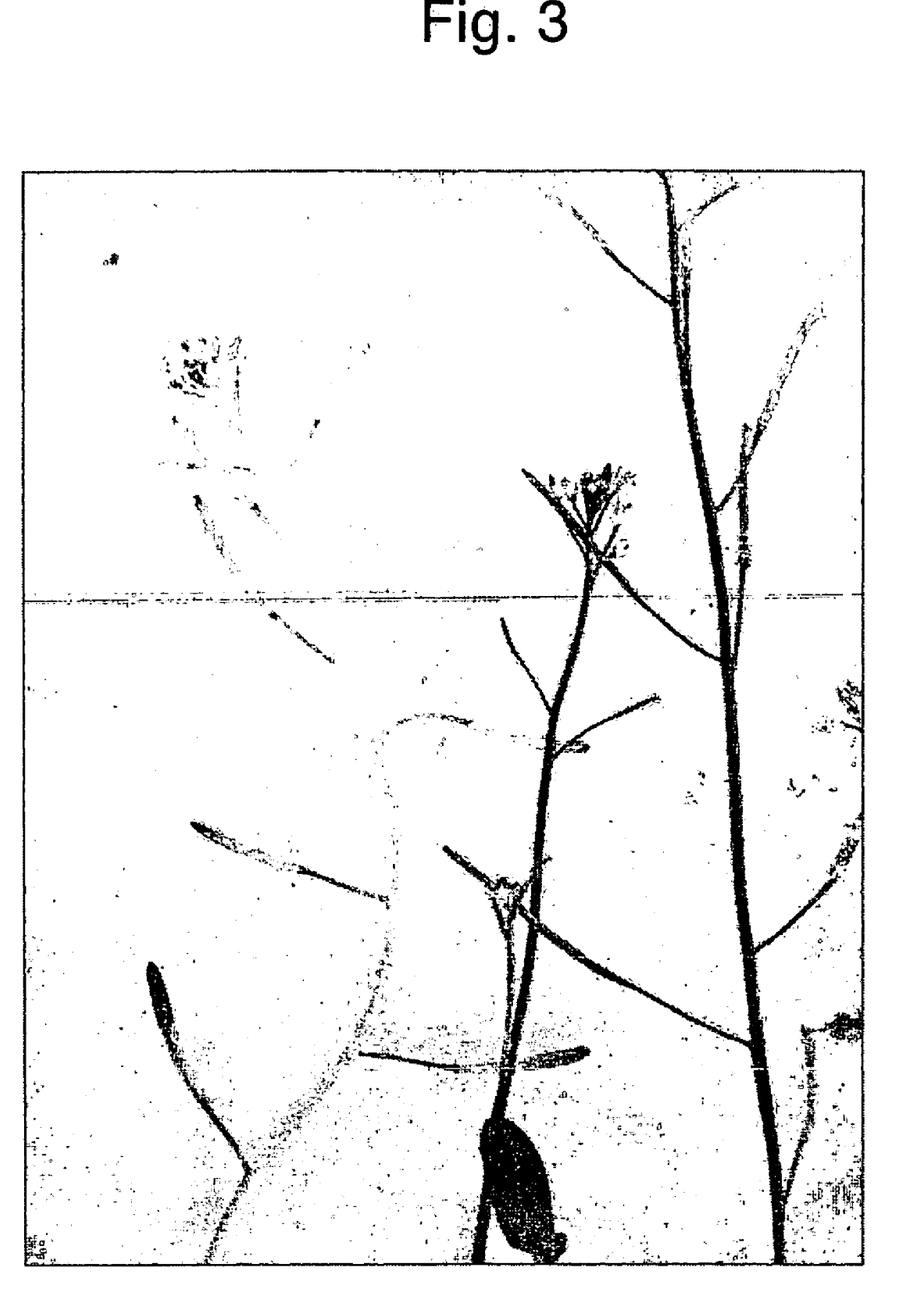
FIG. 3 is a photograph showing a T2 plant body of the F03024 line.
Figure 4:
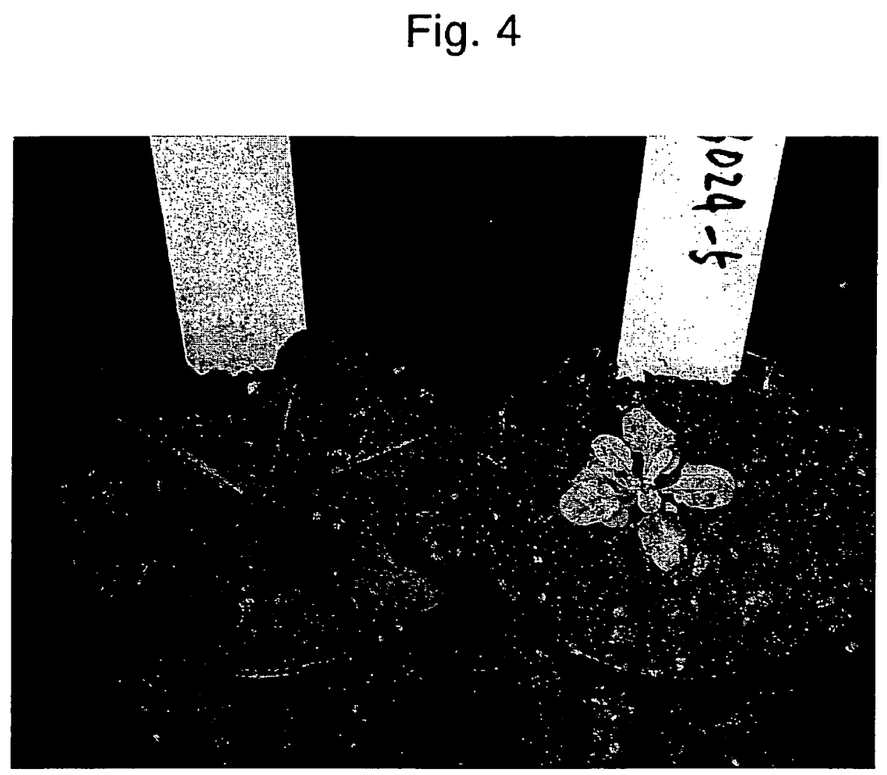
FIG. 4 is a photograph showing a T1 plant body produced by re-introducing F03024 using pBIG03024.

(7) Reconfirmation of Phenotypes and Identification of Gene Functions pBIG03024, one of the plasmids prepared by cloning described above was a plasmid into which a full-length cDNA of approximately 2.4 kb cloned from the F03024 line (shown in FIG. 2) exhibiting a pale green T1 plant body was inserted downstream of a promoter in a sense direction. Further, as shown in FIG. 3, dominant segregation with a ratio of 3:1 was demonstrated in a T2 plant of F03024 in terms of the character of pale green. *Agrobacteria* GV3101 was transformed with pBIG03024. Thereafter, dipping, and selection and breeding of hygromycin-resistant lines were carried out in completely the same manner as the preparation of FOX plants. Then, pale green plants that were completely the same as the T1 line of F03024 were observed in 10 of 21 lines (shown in FIG. 4). Based on this result, cDNA inserted into pBIG03024 was identified as a gene relating to green pigment production in plant.

INDUSTRIAL APPLICABILITY

The system of the present invention enables dominant mutants to be obtained in the same way as in a conventional activation tagging method. In addition, since the number of genes incorporated into a T-DNA is one or two, a gene with over-expression can easily be identified. Further, since the gene is already isolated as a cDNA, further isolation of a causative gene is not necessary and thus a phenotype of the causative gene can easily be reconfirmed and identified using a genomic DNA isolated from a mutant plant. Furthermore, according to the system of the present invention, as long as a full-length cDNA is prepared, the origin of the cDNA is not limited to a specific species of an organism, thereby enabling gene function analysis of various organisms.

Sequence List Free Text

SEQ ID NO: 1 Synthetic DNA

SEQ ID NO: 2 Synthetic DNA

The invention claimed is:

1. A method for analyzing a gene function comprising the steps of:
   (a) preparing a normalized full-length cDNA library containing an expression regulatory sequence by cloning full-length cDNAs from an organism into vectors, sequencing the 5' and 3' terminal sequences of the full-length cDNA clones, selecting all of the full-length cDNA clones that are different from each such that there is no overlapping, and mixing the selected full-length cDNA clones in equivalent amounts;
   (b) infecting a plant group with the normalized full-length cDNA library to introduce the cDNA into the plants;
   (c) selecting a plant complying with desired selection requirements from the plant group having the cDNA introduced thereinto;
   (d) isolating the cDNA from the selected plant; and
   (e) re-introducing the isolated cDNA into a plant of the same species as the plant into which the cDNA has been introduced to reconfirm a phenotype according to the selection requirements.

2. The method according to claim 1, wherein the expression regulatory sequence is a constitutive expression promoter, an inducible promoter, or a combination thereof.

3. The method according to claim 1, wherein the full-length cDNA library is introduced into Agrobacterium.

4. The method according to claim 1, wherein the cDNA is introduced into the plant by infection with Agrobacterium.

5. The method according to claim 1, wherein the selection requirements are based on change of phenotype for stress resistance and/or morphogenesis.

6. The method according to claim 5, wherein the stress is at least one form of stress selected from the group consisting of oligotrophic stress, drought stress, temperature stress, strong light stress, ultraviolet stress, salt stress, air pollution stress, agricultural chemical stress, oxidization stress, heavy metal stress, disease damage stress, and hormone stress.

* * * * *